(12) United States Patent
Tassone et al.

(10) Patent No.: US 8,568,640 B2
(45) Date of Patent: Oct. 29, 2013

(54) METHOD OF MAKING BREAST PROSTHESIS FOR PATIENTS WITH EDEMA

(75) Inventors: Elisabeth C. Tassone, Waldorf, MD (US); Leslie S. Amick, Marietta, GA (US)

(73) Assignee: American Breast Care, LP, Marietta, GA (US)

( * ) Notice: Subject to any disclaimer, the term of this patent is extended or adjusted under 35 U.S.C. 154(b) by 818 days.

(21) Appl. No.: 12/793,173

(22) Filed: Jun. 3, 2010

(65) Prior Publication Data

US 2010/0236687 A1   Sep. 23, 2010

Related U.S. Application Data

(62) Division of application No. 12/101,254, filed on Apr. 11, 2008, now Pat. No. 7,753,954.

(51) Int. Cl.
*B29C 59/00* (2006.01)

(52) U.S. Cl.
USPC ................ 264/248; 264/267; 264/320

(58) Field of Classification Search
None
See application file for complete search history.

(56) References Cited

U.S. PATENT DOCUMENTS

| | | | | |
|---|---|---|---|---|
| 4,531,244 A | * | 7/1985 | Hamas | 623/8 |
| 5,480,429 A | * | 1/1996 | Weber-Unger | 623/7 |
| 5,895,423 A | * | 4/1999 | Becker et al. | 623/7 |
| 2012/0010706 A1 | * | 1/2012 | Schuessler | 623/8 |
| 2013/0131798 A1 | * | 5/2013 | Wollnick et al. | 623/8 |

* cited by examiner

*Primary Examiner* — Edmund H. Lee
(74) *Attorney, Agent, or Firm* — Bryan W. Bockhop; Bockhop & Associates, LLC

(57) ABSTRACT

A breast prosthesis is adapted to massage a patient's chest so as to encourage circulation of interstitial lymph fluid. A breast form member has a front portion that has a shape corresponding to a human breast and a back portion. A protrusion member extends from the back portion. The protrusion member defines at least one protrusion extending outwardly therefrom. The protrusion is disposed so that when the breast prosthesis held against the patient at a preselected location, the protrusion will massage the preselected location, thereby encouraging circulation of interstitial lymph fluid.

7 Claims, 3 Drawing Sheets

METHOD OF MAKING BREAST PROSTHESIS FOR PATIENTS WITH EDEMA

CROSS-REFERENCE TO RELATED APPLICATION(S)

This application is a divisional of, and claims the benefit of, U.S. patent application Ser. No. 12/101,254, filed Apr. 11, 2008, now U.S. Pat. No. 7,753,954, the entirety of which is hereby incorporated herein by reference.

BACKGROUND OF THE INVENTION

1. Field of the Invention

The present invention relates to prosthetic devices and, more specifically, a breast prosthesis that provides massaging action to encourage circulation of lymph fluid.

2. Description of the Related Art

Secondary lymphedema of the upper extremities and upper trunk, usually on the affected (surgical side) is a condition often associated with treatment for breast cancer. Surgery, chemotherapy and radiation treatments damage the lymph nodes of the chest and axilla. The damaged lymph nodes have difficulty moving interstitial lymph fluid. The stagnant fluid can cause painful edema in the chest and arm.

Various products have been used to alleviate the symptoms of lymphedema. One system employs pads that direct lymph fluid flow through channels of ribbed fabric filled with foam. This system is bulky and requires additional coverage, such as a compression garment or sleeve, to hold the pad in the correct location. Another system employs a vest that works in a similar manner, except that the vest is a self-supporting garment. However, the vest must be custom produced and is, therefore, expensive for the end-user. Another alternative method of relieving lymphedema symptoms is to place pieces of foam in specific areas to provide pressure at specific sites on the patient's chest. Such foam requires additional support.

Many women who have had mastectomies wear a breast prosthesis at the affected site. Typically, a breast prosthesis is made to look like a natural breast. It is placed against the patient's chest and is typically supported by a brassiere. Such breast prostheses do little to relieve the symptoms of chest edema.

Therefore, there is a need for a single-piece breast prosthesis that will serve as a prosthesis for the removed breast and also provide a massaging action to encourage flow of lymph fluid.

The disadvantages of the prior art are overcome by the present invention which, in one aspect, is a breast prosthesis adapted to massage a patient's chest so as to encourage circulation of interstitial lymph fluid. A breast form member has a front portion that has a shape corresponding to a human breast and a back portion. A protrusion member extends from the back portion. The protrusion member defines at least one protrusion extending outwardly therefrom. The protrusion is disposed so that when the breast prosthesis held against the patient at a preselected location, the protrusion will massage the preselected location, thereby encouraging circulation of interstitial lymph fluid.

In another aspect, the invention is a mold for making breast prostheses having a front portion and a back portion. A front member has a front mating surface and defines a first cavity opening to the front mating surface. The first cavity has a shape that corresponds to the front portion of the breast prosthesis. A rear member has a rear mating surface, which is complimentary to the front mating surface. The rear member defines a second cavity opening to the rear mating surface. The second cavity has a shape that is complimentary to a shape of at least one prosthesis protrusion that is disposed so that a breast prosthesis cast from the mold will include at least one prosthesis protrusion that is configured to massage a wearer's chest so as to encourage circulation of interstitial lymph fluid in an area of the wearer's chest adjacent to the prosthesis protrusion.

In yet another aspect, the invention is a method of making a breast prosthesis having a front portion and a rear portion, in which a first layer of film is sealed to a second layer of film around a periphery so as to define a first chamber between the first layer of film and the second layer of film. A third layer of film is sealed to the second layer of film so as to define a second chamber between the second layer and the third layer. A first gel is injected into the first chamber. A second gel is injected into the second chamber. The first chamber is placed into a front member of a mold. The front member defines a first cavity that has a shape that corresponds to the front portion of the breast prosthesis. A rear member of the mold is placed on top of the second chamber. The rear member defines a second cavity having a shape that is complimentary to a shape of at least one prosthesis protrusion and that is disposed so that a breast prosthesis cast from the mold will include at least one prosthesis protrusion that is configured to massage a wearer's chest so as to encourage circulation of interstitial lymph fluid in an area of the wearer's chest adjacent to the prosthesis protrusion. The mold is placed in an oven so as to cure the first gel and the second gel and mold the film, thereby forming the breast prosthesis. The breast prosthesis is removed from the oven. The front member of the mold is separated from the rear member of the mold and the breast prosthesis is removed from the mold.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

Figure 1:
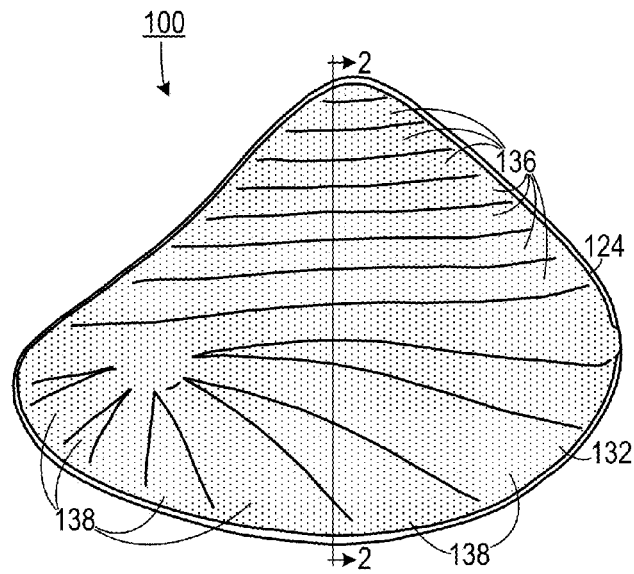
FIG. 1 is a back elevational view of one embodiment of a breast prosthesis.

A preferred embodiment of the invention is now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on."

Figure 2:
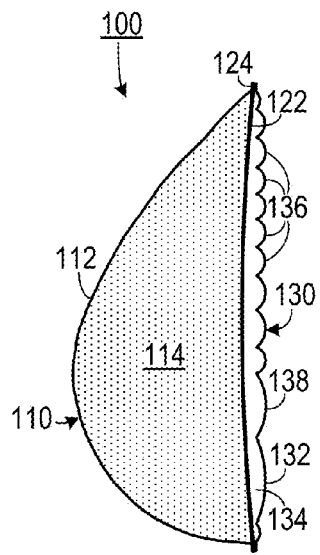
FIG. 2 is a cross-sectional view of the embodiment shown in FIG. 1, taken along line 2-2.
Figure 3:
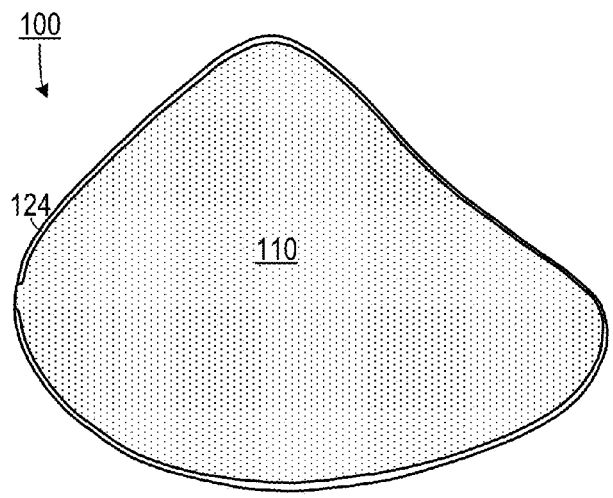
FIG. 3 is a front elevational view of the embodiment shown in FIG. 1.

As shown in FIGS. 1-3, one representative embodiment includes a breast prosthesis 100 adapted to massage a patient's chest so as to encourage circulation of interstitial lymph fluid. The breast prosthesis 100 includes a front breast form member 110 that includes a front portion in a shape corresponding to a human breast. A protrusion member 130 extends from the back of the front breast form member 110. The protrusion member 130 defines a plurality of protrusions (such as a series of parallel latitudinal ribs 136, series of ribs 138 in a rayed pattern issuing from a central location, bumps or other shapes) that extend outwardly from the protrusion member 130 so as to massage the patient's chest when the breast prosthesis 100 is worn against the patient's chest.

Figure 4:
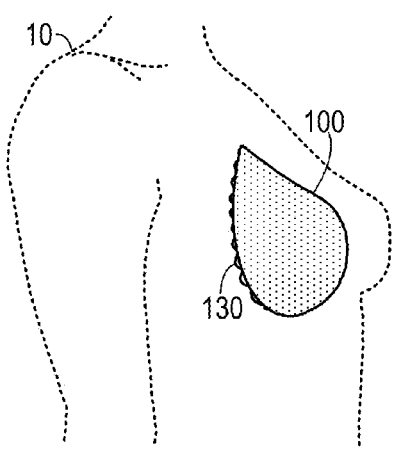
FIG. 4 is a side perspective view of the embodiment shown in FIG. 1 in use.
Figure 5A:
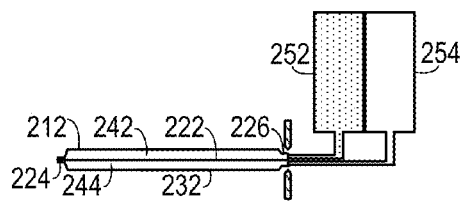
FIGS. 5A-5G are a series of schematic drawings showing one method of making a breast prosthesis.
Figure 5B:
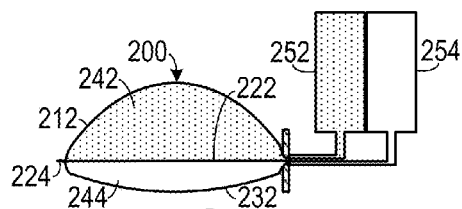
Figure 5D:
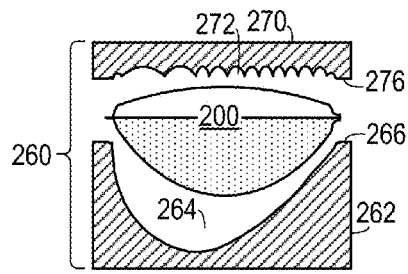
Figure 5C:
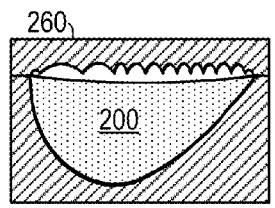
Figure 5E:
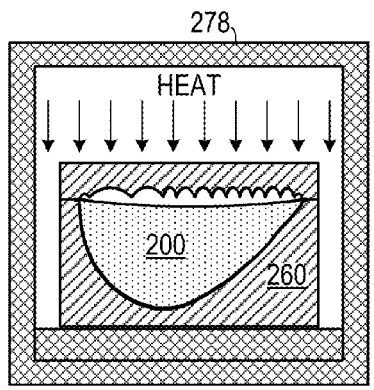
Figures 5F, 5G:
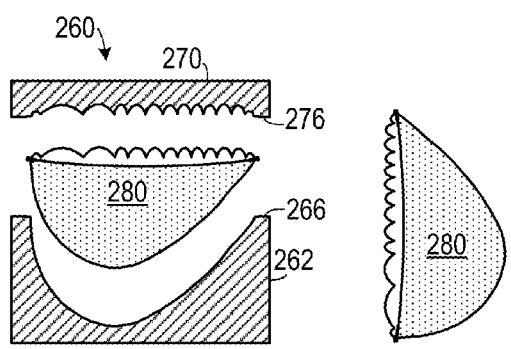

As shown in FIG. 4, the breast prosthesis 100 is typically placed with the protrusion member 130 against the chest of the patient 10 in a mastectomy site and is then held in place by a brassiere (not shown). Once in place, relative movement between the patient 10 and the prosthesis 100 generates a massaging action, which encourages a more natural flow of interstitial lymph fluids in the area around the protrusion member 130.

The breast form member 110 includes a first layer of flexible film 112 and a second layer of flexible film 122 that is sealed to the first layer of flexible film 112 about a periphery 124 so as to define a first chamber 114. Similarly, the protrusion member 130 includes a third layer flexible film 132 that is sealed to the second layer of flexible film 122, also about the periphery 124 so as to define a second chamber 134. The first layer of flexible film 112, the second layer of flexible film 122 and the third layer of flexible film 132 are typically made from a polyurethane film.

The first chamber 114 and the second chamber 134 are both filled with a gel, which is typically a cured silicone gel. Curing of the gel causes the first chamber 114 to maintain the form of a breast and causes the second chamber 134 to maintain the form of the ribs 136 and 138. In one embodiment, the composition of the gel in the second chamber 134 is selected to be firmer than the gel in the first chamber 114. This allows for a natural firmness for the breast form member 110 while increasing the massaging action of the protrusion member 130. In one alternative embodiment, the breast form member and the protrusion member could both be formed as part of a single contiguous chamber. Other gels besides silicone gels could be used, for example TPE, hydrogels and PU gels are examples of gels that may be used in certain embodiments.

As shown in FIGS. 5A-5G, in one method of making a breast prosthesis 280, a first layer of polyurethane film 212, a second layer of polyurethane film 222 and a third layer of polyurethane film 232 are sealed together along a periphery 224 (such as by heat sealing) to form a first chamber 242 and a second chamber 244 (not sealing a portion to allow for an injection sprue 226 into each chamber). The first chamber 142 is injected with an uncured first silicone gel 252 and the second chamber 144 is injected with an uncured second silicone gel 254 and the injection sprues 226 are sealed so as to form a breast prosthesis blank 200.

The breast prosthesis blank 200 is placed inside of a mold 260. The mold 260 includes a front member 262 and a rear member 270. The front member 262 has a front mating surface 266 and defines a first cavity 264 that opens to the front mating surface 266 and has a shape that corresponds to the front portion of the desired breast prosthesis 280. The rear member 270 has a rear mating surface 276 that is complimentary to the front mating surface 266. The rear member 270 defines a second cavity 272 that opens to the rear mating surface 276. The second cavity 272 has a shape that is complimentary to a shape of at least one prosthesis protrusion.

The breast prosthesis blank 200 and the mold 260 are placed in an oven 278 (or other type of heating unit) and maintained at a curing temperature for an amount of time necessary to cure the first silicone gel 252 and the second silicone gel 254 and thermally form or mold the film. Once the gels are cured, the mold 260 and the now formed prosthesis 280 are removed from the oven 278 and allowed to cool. Once cool, the prosthesis is removed from the mold 260, trimmed about the periphery and then washed. The prosthesis 280 is now ready for use.

Figure 6:
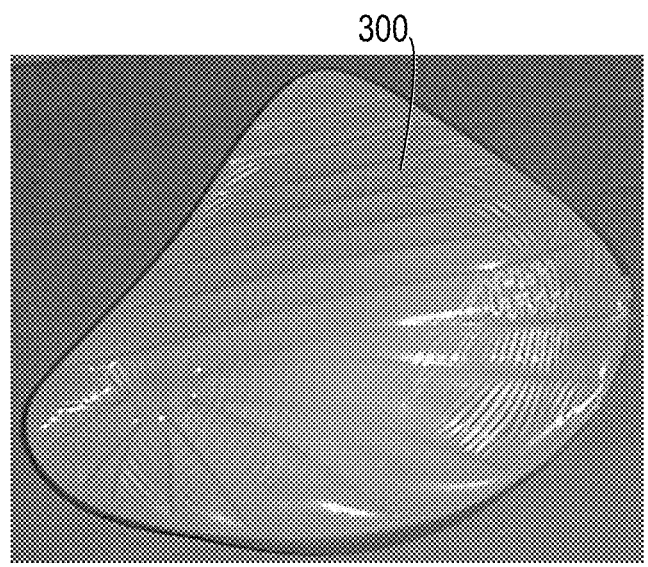
FIG. 6 is a photograph of a back side of a commercial embodiment of a breast prosthesis.

A photograph of one commercial embodiment of a breast prosthesis 300 is shown in FIG. 6. A combination of latitudinal ribs and rayed ribs are employed in this embodiment.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A method of making a breast prosthesis having a front portion and a rear portion, comprising the actions of:
   a. sealing a first layer of film to a second layer of film around a periphery so as to define a first chamber between the first layer of film and the second layer of film;
   b. sealing a third layer of film to the second layer of film so as to define a second chamber between the second layer and the third layer;
   c. injecting a first gel into the first chamber;
   d. injecting a second gel into the second chamber;
   e. placing the first chamber into a front member of a mold in which the front member defines a first cavity that has a shape that corresponds to the front portion of the breast prosthesis;
   f. placing a rear member of the mold on top of the second chamber, in which the rear member defines a second cavity having a shape that is complimentary to a shape of at least one prosthesis protrusion and that is disposed so that a breast prosthesis cast from the mold will include at least one prosthesis protrusion that is configured to massage a wearer's chest so as to encourage circulation of interstitial lymph fluid in an area of the wearer's chest adjacent to the prosthesis protrusion;
   g. placing the mold in an oven so as to cure the first gel and the second gel, thereby forming the breast prosthesis; and
   h. removing the breast prosthesis from the oven, separating the front member of the mold from the rear member of the mold and removing the breast prosthesis from the mold.

2. The method of claim 1, wherein the action of injecting a first gel comprises the action of injecting a first silicone gel.

3. The method of claim 1, wherein the action of injecting a second gel comprises the action of injecting a second silicone gel that is firmer than the first silicone gel.

4. The method of claim 1, wherein the first layer of film, the second layer of film and the third layer of film each comprise a polyurethane film.

5. The method of claim 1, wherein the prosthesis protrusion is disposed to cause lymphatic fluid to flow away from the protrusion when the breast prosthesis is worn against a wearer's chest.

6. The method of claim 5, wherein the prosthesis protrusion comprises a plurality of latitudinal ribs.

7. The method of claim 5, wherein the prosthesis protrusion comprises a rayed pattern of ribs.

* * * * *